United States Patent [19]

Wetzel et al.

[11] 4,364,944
[45] Dec. 21, 1982

[54] CEPHALOSPORINS

[75] Inventors: Bernd Wetzel; Eberhard Woitun, both of Biberach; Wolfgang Reuter, Laupertshausen; Roland Maier, Biberach; Uwe Lechner, Ummendorf; Hanns Goeth, Biberach, all of Fed. Rep. of Germany

[73] Assignee: Dr. Karl Thomae Gesellschaft mit beschränkter Haftung, Biberach, Fed. Rep. of Germany

[21] Appl. No.: 323,382

[22] Filed: Nov. 20, 1981

[30] Foreign Application Priority Data

Dec. 2, 1980 [DE] Fed. Rep. of Germany ....... 3045330
Dec. 2, 1980 [DE] Fed. Rep. of Germany ....... 3045331

[51] Int. Cl.³ .................. A61K 31/545; C07D 501/56
[52] U.S. Cl. ..................................... 424/246; 544/21; 544/22; 544/23; 544/25; 544/27; 544/28
[58] Field of Search ............... 544/27, 22, 21, 25, 544/28; 424/246

[56] References Cited

U.S. PATENT DOCUMENTS 4,316,898 2/1982 Wetzel et al. .................. 544/27

Primary Examiner—Paul M. Coughlan, Jr.
Attorney, Agent, or Firm—Hammond & Littell, Weissenberger & Muserlian

[57] ABSTRACT

Compounds of the formula

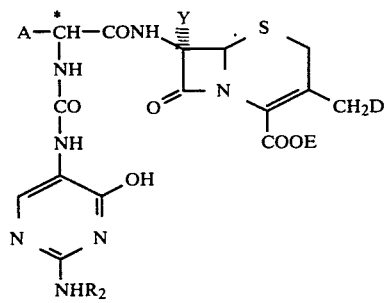

wherein
Y is hydrogen or methoxy;
A is

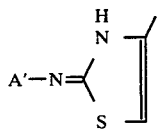

or, when Y is methoxy, also phenyl, 4-hydroxyphenyl, 2-thienyl, 3-thienyl of 3,4-dihydroxy-phenyl;

A' is hydrogen, —COCH$_2$Cl, —COCH$_2$Br, —COOCH$_2$CCL$_3$, formyl or trityl;

D is hydrogen, acetoxy, aminocarbonyloxy, pyridinium, 4-aminocarbonyl-pyridinium or -S-Het, where Het is 3-methyl-1,2,4-thiadiazol-5-yl, 1,2,4-thiadiazol-5-yl, 1,3,4-thiadiazol-5-yl, 2-methyl-1,3,4-thiadiazol-5-yl, 4H-5,6-dioxo-1,2,4-triazine-3-yl, 4-methyl-5,6-dioxo-1,2,4-triazin-3-yl, 1-vinyl-tetrazol-5-yl, 1-allyl-tetrazol-5-yl or

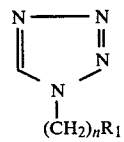

n is 1, 2 or 3;

R$_1$ is hydroxyl, amino, dimethylamino, acetylamino, aminocarbonyl, aminocarbonylamino, aminosulfonyl, aminosulfonylamino, methylcarbonyl, methylsulfonylamino, cyano, hydroxysulfonylamino, methylsulfonyl, methylsulfinyl, a carboxylic acid group or a sulfonic acid group; or —(CH$_2$)$_n$R$_1$ is alkyl of 1 to 4 carbon atoms or 2,3-dihydroxy-propyl;

R$_2$ is unsubstituted or monosubstituted 3-pyridyl, 5-pyrimidinyl, 2-thienyl, 2-furyl-methyl, 2-thienyl-methyl, 2-imidazolyl-methyl, 2-thiazolyl-methyl, 3-pyridyl-methyl or 5-pyrimidinyl-methyl, where the substituent is chlorine, methyl, acetylamino, hydroxyl, methylsulfinyl, methylsulfonyl, aminocarbonyl or aminosulfonyl; and E is hydrogen or a carboxyl-protective group which is easily removable in vitro or in vivo;

and, E is hydrogen, non-toxic, pharmacologically acceptable salts thereof formed with inorganic or organic bases; the compounds as well as their salts are useful as antibiotics.

10 Claims, No Drawings

CEPHALOSPORINS

This invention relates to novel cephalosporins, to methods of preparing these compounds, to pharmaceutical compositions containing them as active ingredients, and to methods of using them as antibiotics.

More particularly, the present invention relates to a novel class of cephalosporins represented by the formula

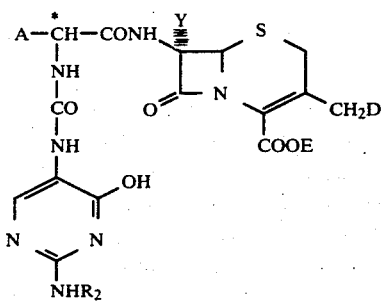

wherein
Y is hydrogen or methoxy;
A is

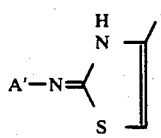

or, when Y is methoxy, also phenyl, 4-hydroxyphenyl, 2-thienyl, 3-thienyl or 3,4-dihydroxy-phenyl;
A' is hydrogen, —COCH$_2$Cl, —COCH$_2$Br, —COOCH$_2$CCl$_3$, formyl or trityl;
D is hydrogen, acetoxy, aminocarbonyloxy, pyridinium, 4-aminocarbonyl-pyridinium or —S—Het, where Het is 3-methyl-1,2,4-thiadiazol-5-yl, 1,2,4-thiadiazol-5-yl, 1,3,4-thiadiazol-5-yl, 2-methyl-1,3,4-thiadiazol-5-yl, 4H-5,6-dioxo-1,2,4-triazin-3-yl, 4-methyl-5,6-dioxo-1,2,4-triazin-3-yl, 1-vinyltetrazol-5-yl, 1-allyltetrazol-5-yl or

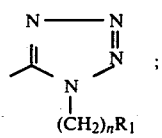

n is 1, 2 or 3;
R$_1$ hydroxyl, amino, dimethylamino, acetylamino, aminocarbonyl, aminocarbonylamino, aminosulfonyl, aminosulfonylamino, methylcarbonyl, methylsulfonylamino, cyano, hydroxysulfonylamino, methylsulfonyl, methylsulfinyl, a carboxylic acid group or a sulfonic acid group; or
—(CH$_2$)$_n$R$_1$ is alkyl of 1 to 4 carbon atoms or 2,3-dihydroxy-propyl;
R$_2$ is an unsubstituted or monosubstituted radical selected from the group consisting of 3-pyridyl, 5-pyrimidinyl, 2-thienyl, 2-furyl-methyl, 2-thienyl-methyl, 2-imidazolyl-methyl, 2-thiazolyl-methyl, 3-pyridyl-methyl or 5-pyrimidinyl-methyl, where the substituent is chlorine, methyl, acetylamino, hydroxyl, methylsulfinyl, methylsulfonyl, aminocarbonyl or aminosulfonyl; and
E is hydrogen or a carboxyl-protective group which is easily removable in vitro or in vivo, such as those which have heretofore been used in the field of penicillins and cephalosporins, especially ester-forming groups which can be removed under mild conditions by hydrogenation or hydrolysis or other treatments, or ester-forming groups which can easily be split off in the living organism;
and, when E is hydrogen, non-toxic, pharmacologically acceptable salts thereof formed with inorganic or organic bases, such as their alkali metal or alkaline earth metal salts, especially sodium, potassium, magnesium or calcium salts; their ammonium salts; or their organic amine salts, especially the triethylamine or dicyclohexylamine salts.

In vitro easily removable protective groups are, for example, benzyl, diphenylmethyl, trityl, tert. butyl, 2,2,2-trichloroethyl or trimethylsilyl.

In vivo easily removable protective groups are, for example, alkanoyloxyalkyl, such as acetoxymethyl, propionyloxymethyl, 2-acetoxyethyl or pivaloyloxymethyl, or phthalidyl.

The asterisk above the carbon atom in formula I indicates a center of asymmetry.

When D is pyridinium or aminocarbonylpyridinium, the compounds of this invention have the formula

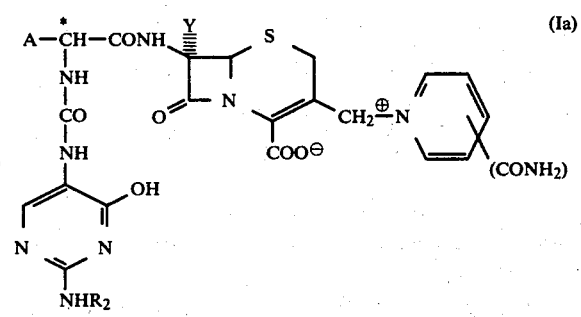

A preferred sub-genus is constituted by compounds of the formula I wherein
A, Y, E and R$_2$ have the same meanings as in formula I;
A' is hydrogen; and
D is acetoxy or —SHet, where Het is 2-methyl-1,3,4-thiadiazol-5-yl, 4-methyl-5,6-dioxo-1,2,4-triazin-3-yl or a radical of the formula II wherein R$_1$ and n have the meanings previously defined;
and, when E is hydrogen, non-toxic, pharmacologically acceptable salts thereof formed with inorganic or organic bases.

The cepalosporin compounds of the formula I and the intermediates described hereinafter exist in two tautomeric forms with respect to the pyrimidine ring, that is, the lactim and the lactam form. Which of the two forms I or I' is predominant, depends particularly on the respective solvent and on the type of substituent —NHR$_2$:

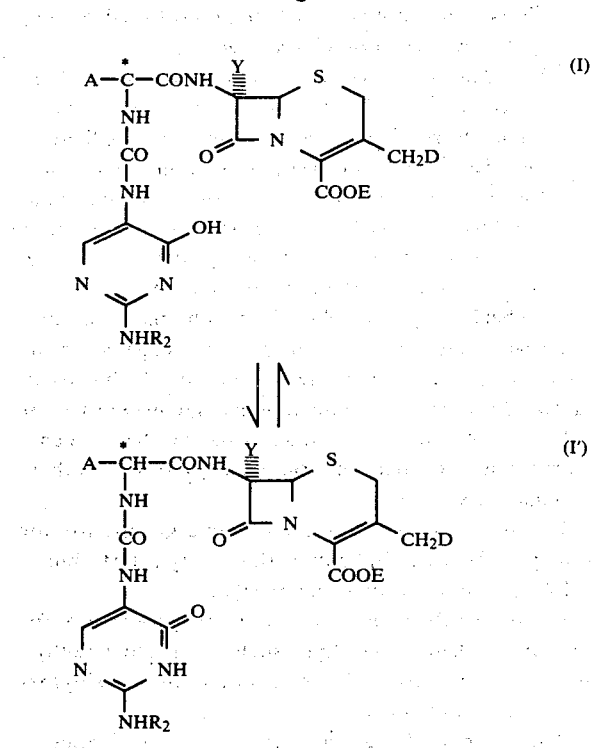

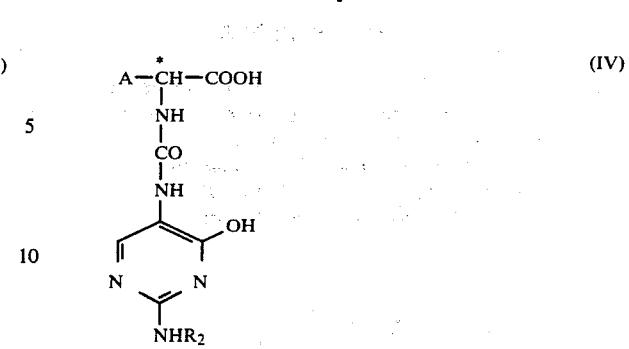

wherein A and $R_2$ have the meanings previously defined, or a salt or reactive derivative thereof.

Suitable reactive derivatives of the ureidocarboxylic acid of the formula IV include, for example, their acid anhydrides such as those derived from chloroformates, for instance ethyl or isobutyl chloroformate, or their reactive esters such as the p-nitrophenyl ester or the N-hydroxysuccinimide ester, or their reactive amides such as the N-carbonyl-imidazole, but also their acid halides such as the corresponding acid chloride or their acid azides.

The ureidocarboxylic acid or a salt or reactive derivative thereof is reacted with the 7-amino-cephalosporanic acid derivative in a solvent at temperatures between $-40°$ C. and $+40°$ C., optionally in the presence of a base. If, for example, an anhydride of the ureidocarboxylic acid, such as the anhydride with ethylchloroformate, is used, the reaction is carried out while cooling, for instance at $-10°$ C. to $+10°$ C. in a solvent such as acetone, tetrahydrofuran, dimethylformamide, chloroform, dichloromethane, hexametapol, or a mixture of these solvents. If, for example, an N-hydroxysuccinimide ester of the ureidocarboxylic acid is reacted with a derivative of the formula III, the reaction is preferably carried out at 0° to 20° C. in the presence of a base such as triethylamine, in a solvent such as dimethylformamide, dichloromethane, dioxane, or a mixture of such solvents.

The reaction of a ureidocarboxylic acid of the formula IV or a salt thereof with a compound of the formula III is advantageously carried out in the presence of a condensation agent, for instance in the presence of N,N'-dicyclohexyl-carbodiimide.

Likewise, when A is aminothiazolyl, the following tautomeric forms may occur with respect to that ring system:

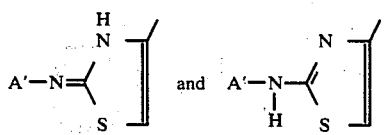

It goes without saying that the compounds of the formula I referred to above always comprise both tautomeric forms.

With regard to the chiral center C*, the compounds of the formula I may be present in the two possible R- and S-configurations or as mixtures of these.

The compounds of the formula I may be prepared by the following methods:

Method A

By reacting a 7-amino-cephalosporanic acid compound of the formula

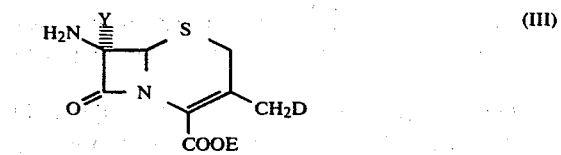

wherein
E and Y have the meanings previously defined, and
D is hydrogen, acetoxy, aminocarbonyl or —SHet, with a ureidocarboxylic acid of the formula

Method B

By reacting a 7-amino-cephalosporanic acid of the formula

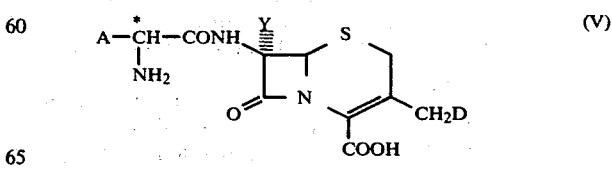

wherein A, Y and D have the meanings previously defined, with a pyrimidine derivative of the formula

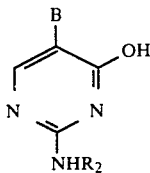

wherein
R₂ has the meanings previously defined, and
B is —NCO or a reactive derivative of —NHCOOH, such as —NHCOCl, —NHCOBr or

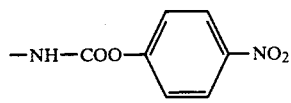

where —NCO and —NHCOCl are especially preferred.

Also mixtures of such pyrimidine derivatives of the formula VI can be used, wherein B has partly the one and partly the other of the above-mentioned meanings, for instance =NCO and —NHCOCl simultaneously.

The reaction is preferably carried out in any desired mixtures of water and those organic solvents which are miscible with water such as ketones, for example acetone; cyclic ethers, for example tetrahydrofuran or dioxane; nitriles, for example acetonitrile; formamides, for example dimethylformamide; dimethylsulfoxide; or alcohols, for example isopropanol; or in hexametapol. By addition of a base or by use of a buffer solution, the pH of the reaction mixture is kept in a pH range of about 2.0 to 9.0, preferably between pH 6.5 and 8.0.

Method C

By reacting a compound of the formula

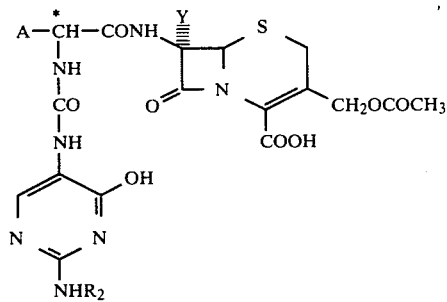

wherein A, R₂ and Y have the meanings previously defined, either with a compound of the formula Het—S—M                                  (VIII)

wherein
Het has the meanings previously defined, and
M is hydrogen, an alkali metal or an alkaline earth metal,
or with pyridine or 4-amino-carbonyl-pyridine.

A compound of the formula I, wherein D is —SHet, pyridinium or 4-aminocarbonylpyridinium, and E is hydrogen, is obtained.

For example, a compound of the formula VII is reacted with 1-methyl-5-mercapto-1,2,3,4-tetrazole in a solvent such as water, methanol, ethanol, acetone, methyl ethyl ketone, tetrahydrofuran, acetonitrile, ethyl acetate, dimethoxyethane, dimethylformamide, dimethyl sulfoxide, chloroform or a mixture of these solvents. Preferably, a strong polar solvent such as water or the like is used. In this case the pH of the reaction solution is advantageously maintained between 2 and 10, and particularly between 4 and 8. The desired pH-value can be adjusted by addition of a buffer solution, such as sodium phosphate. The reaction conditions are not subject to special restrictions. Normally, the reaction is carried out at a temperature in a range of 0° to 100° C., over a reaction time of several hours.

Method D

A compound of the formula I wherein Y is methoxy can also be obtained by reacting a compound of the formula I, wherein Y is hydrogen, in the presence of methanol with an alkali metal methylate of the formula M⁺OCH₃⁻, where M⁺ is an alkali metal, and then with a halogenating agent. For this purpose, a cephalosporin of the formula I wherein Y is hydrogen is dissolved or suspended in an inert solvent, such as tetrahydrofuran, dioxane, ethyleneglycol dimethylether, methylene chloride, chloroform, dimethyl formamide, methanol or the like or in a mixture of two of these solvents.

An alkali metal methylate together with methanol is added to the obtained solution or suspension. The obtained mixture is caused to react, and the reaction mixture is then reacted with a halogenating agent. In this reaction methanol is used in excess, and the quanity of the alkali metal methylate is preferably 2 to 6 equivalents per equivalent of cephalosporin. "Excess" means an amount of more than one equivalent per equivalent of cephalosporin. All reactions are carried out at temperatures between −120° and −10° C., and preferably between −100° and −50° C. A reaction time of 5 to 60 minutes is sufficient. The reaction is terminated by acidifying the reaction system.

The halogenating agent used in this method is generally known as a source for positive halogen atoms, such as Cl⁺, Br⁺ or I⁺. Examples of such halogenating agents are halogens, such as chlorine, bromine etc., N-halo-imides, such as N-chloro-succinimide, N-bromo-succinimide, and the like; N-halo-amides, such as N-chloro-acetamide, N-bromo-acetamide, etc.; N-halo-sulfonamides, such as N-chloro-benzene-sulfonamide, N-chloro-p-toluene-sulfonamide, etc., 1-halo-benzotriazoles; 1-halotriazines; organic hypohalites, such as tert. butylhypochlorite, tert. butylhypoiodite, etc., and halo-hydantoins, such as N,N-dibromo-hydantoin, etc. Tert. butylhypochlorite is preferred among these halogenating agents. The halogenating agent is used in a quantity sufficient to produce an equivalent quantity of positive halogen atoms with regard to the amount of cephalosporin of the formula I.

Suitable acids for termination of the reaction are those which do not lead to solidification of the reaction mixture or to freezing of the reaction mixture into a heavy viscous mass when they are added to the cold reaction mixture. Suitable acids are, for example, 98% formic acid, glacial acetic acid, trichloroacetic acid or methane sulfonic acid.

After the termination of the reaction the excess halogenating agent is removed by treatment with a reducing agent such as trialkyl phosphite, sodium thiosulfate or the like.

The compounds prepared according to methods A, B, C and D, wherein E is other than hydrogen, can be converted accordng to known methods in cephalosporin chemistry into the free carboxylic acids of the formula I wherein E is hydrogen, which are particularly preferred end products. Thus, a silyl protective group can, for example, be easily removed by aqueous hydrolysis, and a diphenylmethyl group can be removed, for example, by cleavage with anisole and trifluoroacetic acid. These methods of elimination of the protective groups are known from the literature.

The compounds of the formula I wherein A is aminothiazolyl and A' is other than hydrogen prepared according to the above processes, can be treated in known manner in order to separate the imino protective group. In this way the compounds wherein A' is hydrogen, which are particularly preferred end products according to the invention, are obtained. For example, a compound of the formula I wherein A is aminothiazolyl, A' is chloroacetyl and E is diphenylmethyl is first treated with thiourea in order to separate the chloroacetyl group and is then treated in known manner with anisole and trifluoroacetic acid to separate the protective ester group (cf. also German Offenlegungsschrift No. 2,924,296), or the protective ester group may be separated with sodium N-methyl-dithiocarbamate (cf. published European patent application No. 2586).

The compounds of the formula I wherein E is a sodium or potassium cation are prepared by reacting the corresponding free acid of the formula I, i.e. wherein E represents hydrogen, with the corresponding salt-forming ion. Suitable methods of doing this include, for example, the reaction with sodium ethyl-hexanoate conventionally used in the chemistry of penicillins and cephalosporins, or the reaction with sodium carbonate with subsequent freeze-drying. The cephalosporin antibiotics of the formula I wherein E is hydrogen may be converted in known manner into the corresponding acyloxyalkyl esters, wherein E is, for example, pivaloyloxymethyl of the formula

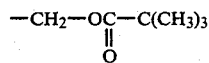

by reacting an alkali metal salt of the cephalosporin carboxylic acid, for example a sodium or potassium salt, with a pivaloyloxymethyl halide of the formula

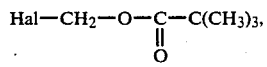

wherein Hal is chlorine, bromine or iodine. Other suitable acyloxyalkyl halides include, for example, chloromethyl acetate, bromomethyl propionate or 1-bromoethyl acetate.

By using the corresponding starting compounds, it is possible to prepare the compounds of the formula I in the form of racemates or in the form of the individual isomers. If the end product is obtained in the D,L form, the pure D- and L-diastereoisomers may be isolated by preparative liquid chromatography (HPLC). The present invention includes the racemates and the isomers.

The ureidocarboxylic acid derivatives of the formula IV, where A is other than aminothiazolyl, are known from the literature. They are described in German Offenlegungsschrift No. 2,924,296. When A is aminothiazolyl, they may be obtained by reacting the amino acid derivative of the formula

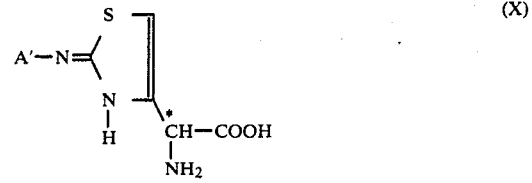

or a salt thereof formed with an acid such as $CF_3COOH$, with a pyrimidine derivative of the formula VI.

The reaction is carried out at temperatures between $-20°$ and $+40°$ C., preferably between $0°$ and $+20°$ C., in a solvent. Suitable solvents include, for example, mixtures of water and organic solvents which are miscible with water, such as acetone, tetrahydrofuran, dioxane, acetonitrile, dimethylformamide, ethanol or dimethylsulfoxide. It may be necessary to use a hydrogen halide-binding agent; suitable such agents include, for example, trialkylamines such as triethylamine, or inorganic bases such as dilute sodium hydroxide.

The starting compounds of the formula VI may be obtained, for example, by reacting a corresponding 5-aminopyrimidine of the formula

wherein $R_2$ has the meanings previously defined, with phosgene. This reaction is preferably carried out in a solvent which does not contain hydroxyl groups, such as tetrahydrofuran, methylene chloride, chloroform, dimethoxyethane or hexametapol at temperatures between $-40°$ and $+60°$ C., preferably between $-10°$ and $+20°$ C. It is advisable to bind the resulting hydrogen chloride with an equimolar amount of an inert organic base, such as triethylamine or pyridine. Pyridine in excess may also be used as the solvent. If the particular aminopyrimidine of the formula XI does not dissolve readily in one of the above-mentioned solvents, phosgenation may also be effected in the heterogeneous phase. Moreover, in a particularly preferred embodiment, an aminopyrimidine of the formula XI may be converted, by treating it with a silylating agent such as hexamethyldisilazane, trimethylchlorosilane/triethylamine, trimethylsilyldiethylamine or N,O-bis-trimethylsilylacetamide, into an aminopyrimidine which is generally very readily soluble in the above-mentioned solvents and which is mono- or polysilylated, depending on the exchangeable hydrogen atoms present, and which then reacts with phosgene to form the corresponding compound of the formula VI; this reaction is preferably carried out without the addition of a base. Depending on the type of solvent, the temperature, the amount and nature of the base which is used, either the corresponding isocyanate or carbamic acid halide is predominantly formed. Depending on the conditions, the isocyanate of the formula VI is also partially or entirely present as a dihydro-oxazolo[(5,4-d]-pyrimidin-2-one of the formula

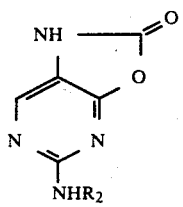

(VIa)

which is isomeric to the isocyanate, or as a mono- or polysilylated analog, depending on the nature of the substituent $R_2$.

The starting compounds of the formula VI obtained by phosgenation, or the mixtures or silyl products thereof, are generally readily soluble in the above-mentioned solvents and, after removal of the excess phosgene, can be reacted directly, without further purification, with the corresponding cephalosporin derivatives of the formula V. However, it is also possible to isolate the intermediate product of the formula VIa, desilylate it with a protic solvent, such as with methanol or water, if required, purify it on the basis of its solubility characteristics, and react it in the manner described above.

Methods of synthesis for 2-substituted 5-amino-4-hydroxy-pyrimidines of the formula XI are, in principle, know from the literature. Special examples are described in German Offenlegungsschrift No. P 2,928,344. The synthesis of starting compounds of the formula V is known from the literature. For example, if A is aminothiazolyl, a cephalosporin derivative of the formula III is reacted with an amino acid of the formula X which is protected at the amino group under the conditions conventionally used in cephalosporin chemistry, and then the protective groups are removed as usual (cf. German Offenlegungsschrift No. 2,924,296).

The 7-amino-cephalosporanic acid derivatives of the formula III are described in the literature.

The cephalosporins of the formula VII can be prepared by the methods described in the examples below.

The preparation of the cephalosporins of the formula IX used as starting materials is, when A is aminothiazolyl, also described in the examples below. When A is other than aminothiazolyl, their preparation is described in German Offenlegungsschrift Nos. 2,928,344 or 3,047,082.

The following examples illustrate the present invention and will enable others skilled in the art to understand it more completely. It should be understood, however, that the invention is not limited solely to the particular examples given below.

I. Synthesis of ureidocarboxylic acids of the formula IV. For A=aminothiazolyl:

EXAMPLE A

D,L-α-{3-[2-(5'-sulfamoyl-2'-thienylmethylamino)-4-hydroxy-5-pyrimidinyl]-ureido}-(2,3-dihydro-2-imino-4-thiazolyl)-acetic acid 1.73 gm of D,L-α-amino(2,3-dihydro-2-imino-4-thiazolyl)-acetic acid (0.01 mol) were dissolved with 10 ml of 1 N sodium hydroxide in a mixture of 60 ml of tetrahydrofuran and 20 ml of water (solution I).

3.01 gm of 5-amino-2-(5'-aminosulfonyl-2'-thienylmethylamino)-4-hydroxy-pyrimidine (0.01 mol) were suspended in 50 ml of dry tetrahydrofuran, and the suspension was refluxed with 6 ml of diethylamino-trimethysilane until a solution was formed. The solution was evaporated to dryness in vacuo, dissolved again in 50 ml of tetrahydrofuran, and this solution was added dropwise, while cooling with ice, to a solution of 1.05 gm of phosgene in 20 ml of dry tetrahydrofuran. The mixture was stirred for 15 minutes while cooling with ice, and was then evaporated in vacuo to half its volume.

This solution was added dropwise to solution I prepared above, while cooling with ice; the pH was maintained at 8.0. The cooling means were removed, and the mixture was stirred for one hour at room temperature. It was then diluted with 30 ml of water, and the tetrahydrofuran was removed in vacuo. The aqueous phase was extracted twice with ethyl acetate and then adjusted to pH 3.8 with 2 N hydrochloric acid. The precipitate formed thereby was suction-filtered off and dried in vacuo.

Yield: 3.12 gm (62% of theory).

IR-spectrum: 3300 (broad), 1640–1650, 1530 (broad signal), 1155 cm$^{-1}$.

NMR-spectrum (DMSO+CD$_3$OD) signals at ppm: 4.65 (s, broad, 2H), 5.15 (s, 1H), 6.5 (s, 1H), 7.05 (d, 1H), 7.45 (d, 1H), 8.15 (s, 1H).

The ureidocarboxylic acids of the formula IV shown in the following table were synthesized analogously (A'-hydrogen):

| Example | $R_2$ | Yield in % | NMR-Spectrum (DMSO + CD$_3$OD) Signals at ppm: |
|---------|-------|------------|-------------------------------------------------|
| B | pyridyl-CH$_2$— | 56 | 4.5 (broad, 2H), 5.15 (s, 1H), 6.45 (s, 1H), 7.25 (m, 1H), 7.7 (m, 1H), 8.1 (s, 1H), 8.5 (m, 2H). |
| C | furyl-CH$_2$— | 64.5 | 4.4 (s, 2H), 5.10 (s, 1H), 6.3 (m, 2H), 6.5 (s, 1H), 7.5 (s, 1H), 8.05 (s, 1H). |
| D | HO-pyridyl- | 41 | 5.2 (s, 1H), 6.4 (s, 1H), 6.55 (s, broad 1H), 7.55 (q, 1H), 7.8 (d, 1H), 8.2 (s, 1H). |
| E | CH$_3$-imidazolyl-CH$_2$— | 58 | 2.1 (s, 3H), 4.4 (s, 2H), 5.15 (s, 1H), 6.80 (s, 1H), 7.3 (s, 1H), 8.05 (s, 1H). |
| F | CH$_3$-pyrimidinyl-CH$_2$— | 60 | 2.5 (s, 3H), 4.4 (s, 2H), 5.15 (s, 1H), 6.40 (s, 1H), 8.05 (s, 1H), 8.6 (s, 2H). |

II. Synthesis of cephalosporins of the formula I

EXAMPLE 1

Sodium 7β-{D,L-α-[3-(4-hydroxy-2-(3'-pyridylmethylamino)-5-pyrimidinyl)-ureido]-2,3-dihydro-2-imino-4-thiazolyl)-acetamido}-3-[(1-methyl-tetrazol-5-yl)-thiomethyl]-ceph-3-em-4-carboxylate 2.08 gm (0.005 mol) of the ureidocarboxylic acid of Example B were dissolved in 50 ml of dry dimethylformamide. 2.5 gm of sodium 7-amino-3-[(1-methyl-tetrazol-5-yl)-thiomethyl]-ceph-3-em-4-carboxylate, dissolved in 30 ml of methylene chloride, were added, and 1.15 gm of N,N'-dicyclohexyl-carbodiimide were added while cooling with ice.

The mixture was stirred overnight while cooling with ice, then evaporated to dryness in vacuo and the residue was extracted first with 50 ml of methanol and then with 100 ml of methylene chloride. After suction-filtering, the solid product was chromatographed on a silicagel column to remove minor impurities (eluant: methylene chloride/methanol 5:1).

The diphenylmethylester thus obtained was cleaved with 10 ml of trifluoroacetic acid and 4 ml of anisole in the usual way, and the free acid was converted into the sodium salt with sodium ethyl hexanoate in dimethylformamide/methanol.

Yield: 1.90 gm (31%).

IR-spectrum: 3340, 1765, 1660, 1540 cm$^{-1}$.

NMR-spectrum (DMSO+CD$_3$OD) signals at ppm: 3.50 (m, 2H), 3.95 (s, 3H), 4.4 (m, 4H), 5.0 (m, 1H), 5.4 (s, 1H), 5.6 (m, 1H), 6.45 (d, 1H), 7.25 (m, 1H), 7.65 (m, 1H), 8.1 (s, 1H), 8.5 (m, 2H).

The following cephalosporins of general formula I (A'=hydrogen, E=sodium ion, Y=hydrogen) were synthesized in analogous manner:

| Example | R$_2$ | D | Yield % | IR-Spec: cm$^{-1}$ | NMR-Spectrum (DMSO + CD$_3$OD) Signals at ppm: |
|---|---|---|---|---|---|
| 2 | 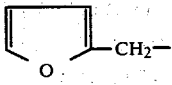 | 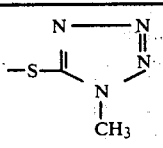 | 56 | 1765 1660 1540 | 3.50 (m, 2H), 3.95 (s, 3H), 4.4 (m, 4H), 5.05 (m, 1H), 5.40 (s, 1H), 5.65 (m, 1H), 6.3 (m, 2H), 6.45 (d, 1H), 7.5 (s, 1H), 8.05 (s, 1H). |
| 3 | 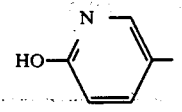 | 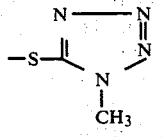 | 38 | 1765 1655 1545 | 3.55 (m,2H), 3.95 s,3H), 4.4 (m,2H), 5.05 (m,1H), 5.35 (s,1H), 5.60 (m,1H), 6.45 (s,1H), 6.55 (s,1H, broad), 7.55 (q,1H), 7.8 (d,1H), 8.2 (s,1H). |
| 4 | 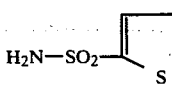 | 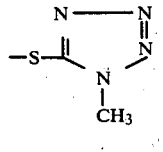 | 61 | 1765 1660 1540 1160 | 3.55 (m,2H), 3.95 (s,3H), 4.4 (m,2H), 4.7 (s,2H), 5.0 (m,1H), 5.35 (s,1H), 5.6 (m,1H), 6.45 (d,1H), 7.05 (d,1H), 7.45 (d,1H), 8.15 (s,1H). |
| 5 | 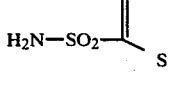 | —O—COCH$_3$ | 48.5 | 1765 1655 1530 1155 | 2.05 (s,3H), 3.50 (m,2H), 4.7 (s,2H), 4.85–5.05 (m,2+1H), 5.40 (s,1H), 5.65 (m,1H), 6.45 (broad s,1H), 7.05 (d,1H), 7.45 (d,1H), 8.15 (s,1H). |
| 6 |  | 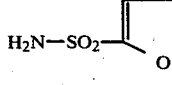 | 49 | 1765 1700 1670 | 3.3 (s,3H), 3.60 (m,2H), 4.2 (m,2H), 4.65 (s,2H), 5.0 (d,1H), 5.40 (s,1H), 5.65 (broad m,1H), 6.45 (s,1H), 7.0 d,1H), 7.45 (d,1H), 8.15 (s,1H). |
| 7 | 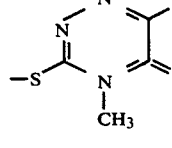 | 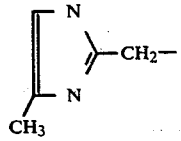 | 44 | 1765 1650 1520 | 2.1 (s,3H), 3.50 (m,2H), 3.95 (s,3H), 4.4 (m,4H), 5.05 (broad d,1H), 5.40 (s,1H), 5.60 (m,1H), 6.80 (s,1H), 7.3 (s,1H), 8.05 (s,1H). |
| 8 | 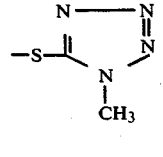 | 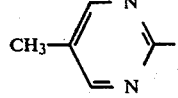 | 49.5 | 1765 1655 1540 | 2.45 (s,3H), 3.45 (m,2H), 3.95 (s,3H), 4.3–4.5 (m,4H), 5.0 (m,1H), 5.40 (s,1H), 5.65 (m,1H), 6.45 (broad s,1H), 8.10 (s,1H), 8.55 (s,2H). |

EXAMPLE 9

Sodium
7α-methoxy-7β-{D,L-α-[3-(2-(5'-sulfamoyl-2'-thienylmethylamino)-4-hydroxy-5-pyrimidinyl)-ureido]-2,3-dihydro-2-imino-4-thiazolyl)-acetamido}-3-[(1-methyl-tetrazol-5-yl)-thiomethyl]-ceph-3-em-4-carboxylate 1.8 gm (0.002 mol) of the diphenylmethyl ester of the cephalosporin of Example 4 were dissolved in 70 ml of dry tetrahydrofuran. At −70° C., a solution of 500 mg of lithium methoxide in 20 ml of dry methanol was added, and the mixture was stirred at this temperature for 3 minutes. Then, at −70° C., 300 mg of t.butyl-hypochlorite were added. The mixture was stirred at −70° C. for 45 minutes, and then 0.6 ml of glacial acetic acid and 150 mg of triethylphosphite were added thereto. 100 ml of phosphate buffer (pH 7.0) were added at room temperature, and the mixture was extracted three times with methylene chloride. The organic phase was separated and dried, and the solvent was evaporated in vacuo. The residue was chromatographed twice on a silica-gel column (eluant: methanol/methylene chloride 1:6). 530 mg of the desired diphenylmethyl ester were obtained (30% of theory).

The product was cleaved to produce the free acid, which was converted into the sodium salt as described in Example 1.

IR-spectrum: 1765, 1670, 1155 cm$^{-1}$.

NM-spectrum (DMSO+CD$_3$OD) signals at ppm: 3.40 (s, 3H), 3.55 (m, 2H), 3.95 (s, 3H), 4.35 (m, 2H), 4.7 (s, 2H), 5.05 (broad s, 1H), 5.35 (s, 1H), 6.45 (d, 1H), 7.05 (d, 1H), 7.45 (d, 1H), 8.15 (s, 1H).

EXAMPLE 10

Sodium
7α-methoxy-7β-{D,L-α-[3-(2-(5'-sulfamoyl-2'-thienylmethylamino)-4-hydroxy-5-pyrimidinyl)-ureido]-(2,3-dihydro-2-imino-4-thiazolyl)-acetamido}-3-{[1-(2'-hydroxyethyl)-tetrazol-5-yl]-thiomethyl}-ceph-3-em-4-carboxylate 1.0 gm (1.5 mmol) of 7α-methoxy-7β-[(D,L-α-amino)-2,3-dihydro-2-imino-4-thiazolyl)-acetamido]-3-{[1-(2'-hydroxyethyl)-tetrazol-5-yl]-thiomethyl}-ceph-3-em-4-carboxylic acid trifluoroacetate were dissolved in a mixture of 60 ml of tetrahydrofuran and 20 ml of water. The pH of the solution was adjusted to 8.5 by the addition of 1 N sodium hydroxide.

450 mg of 5-amino-4-hydroxy-2-(5-sulfamoyl-thienyl-methylamino)-pyrimidine were silylated in the usual way and reacted with 150 mg of phosgene. The resulting mixture was added to the solution of the cephalosporin, while the pH was maintained between 7.5 and 8.0 with sodium hydroxide. After the mixture had been added, the resulting mixture was stirred for another hour at room temperature. Then, another 10 ml of water were added, the insoluble matter was filtered off, and the tetrahydrofuran was evaporated in vacuo. The aqueous phase was extracted twice with ethyl acetate and then adjusted to pH 3.5 with dilute hydrochloric acid while cooling with ice. The precipitate formed thereby was suction-filtered off, dried and converted into the sodium salt in the usual way.

Yield: 655 mg (44.5%).

IR-spectrum: 1765, 1775 cm$^{-1}$.

NMR-spectrum (DMSO+CD$_3$OD) signals at ppm: 3.43 (s,3H), 3.7 (m, 2H), 4.3 (m, 2+2+2H), 4.65 (s, 2H), 5.1 (s, broad, 1H), 5.4 (s, 1H), 6.5 (s, 1H), 7.05 (d, 1H), 7.4 (d, 1H), 8.13 (s, 1H).

The following 7α-methoxy-cephalosporins were synthesized analogous to Example 9:

EXAMPLE 11

Sodium 7α-methoxy-7β-{D,L-α-[3-(4-hydroxy-2-(3'-pyridylmethylamino)-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylate Yield: 36.5% (of theory).

IR-spectrum: 1765, 1660, 1540 cm$^{-1}$.

NMR-spectrum (DMSO+CD$_3$OD) signals at ppm: 3.40 (s, 3H), 3.55 (m, 2H), 3.95 (s, 3H), 4.4 (m, 4H), 5.0 (s, broad, 1H), 5.35 (s, 1H), 6.45 (s. broad, 1H), 7.25 (m, 1H), 7.65 (m, 1H), 8.1 (s, 1H), 8.5 (m, 2H).

EXAMPLE 12

Sodium
7α-methoxy-7β-{D,L-α-[3-(4-hydroxy-2-(4'-methyl-2'-imidazolyl-methylamino)-5-pyrimidinyl)-ureido]-(2,3-dihydro-2-imino-4-thiazolyl)-acetamido}-2-[(1-methyl-tetrazol-5-yl)-thiomethyl]-ceph-3-em-4-carboxylate Yield: 34% of theory.

IR-spectrum: 1765, 1655, 1535 cm$^{-1}$.

NMR-spectrum (DMSO+CD$_3$OD) signals at ppm: 2.1 (s, 3H), 3.40 (s, 3H), 3.50 (m, 2H), 3.95 (s, 3H), 4.4 (m, 4H), 5.0 (s, 1H), 5.35 (s, 1H), 6.85 (d, 1H), 7.3 (s, 1H), 8.05 (s, 1H).

EXAMPLE 13

Sodium
7β-{D,L-α-[3-(2-(5'-sulfamoyl-2'-thienylmethylamino)-4-hydroxy-5-pyrimidinyl)-ureido]-(2,3-dihydro-2-imino-4-thiazolyl)-acetamido}-3-{[1-(2'-hydroxyethyl)-tetrazol-5-yl]-thiomethyl}-ceph-3-em-4-carboxylate 600 mg of the cephalosporin of Example 5 were heated at 80° C. with 220 mg of 1-(2'-hydroxyethyl)-5-mercapto-tetrazole in 40 ml of nitromethane for 6 hours. The mixture was then evaporated to dryness in vacuo. The residue was dissolved in a mixture of acetone and ethyl acetate. While cooling with ice, diphenyldiazomethane was added until the violet color was maintained. The residue was purified by column chromatography (silicagel; eluant: methylenechloride/methanol 5:1). The ester thus obtained was cleaved in the usual way, and the acid was converted into the sodium salt.

Yield: 280 mg (43% of theory).

IR-spectrum: 1765, 1660, 1540, 1155 cm$^{-1}$.

NMR-spectrum (DMSO+CD$_3$OD) signals at ppm: 3.55 (m, 2H), 4.1–4.7 (m, 8H), 5.05 (m, 1H), 5.35 (s, 1H), 5.60 (m, 1H), 6.45 (broad, s, 1H), 7.05 (d, 1H), 7.45 (d,1H), 8.15 (s, 1H).

The following compounds were prepared analogously:

EXAMPLE 14

Sodium
7β-{D,L-α-[3-(2-(5'-sulfamoyl-2'-thienylmethylamino)-4-hydroxy-5-pyrimidinyl)-ureido]-(2,3-dihydro-2-imino-4-thiazolyl)-acetamido}-3-[2-methyl-1,3,4-thiadiazol-5-yl)-thiomethyl]-ceph-3-em-4-carboxylate Yield: 46.5% of theory.

IR-spectrum: 1765, 1660, 1535, 1160 cm$^{-1}$.

NMR-spectrum (DMSO+CD₃OD) signals at ppm: 2.75 (s, 3H), 3.50 (m, 2H), 4.25 (m, 2H), 4.65 (s, 2H), 5.05 (m, 1H), 5.40 (s, 1H), 5.60 (m, 1H), 6.45 (d, 1H), 7.05 (d, 1H), 7.45 (d, 1H), 8.10 (s, 1H).

EXAMPLE 15

Sodium 7β-{D,L-α-[3-(2-(5'-sulfamoyl-2'-thienylmethylamino)-4-hydroxy-5-pyrimidinyl)-ureido]-(2,3-dihydro-2-imino-4-thiazolyl)-acetamido}-3-{[1-(2'-acetylaminoethyl)-tetrazol-5-yl]-thiomethyl}-ceph-3-em-4-carboxylate Yield: 42% of theory.
IR-spectrum: 1760, 1655, 1610 cm⁻¹.
NMR-spectrum: 1.85 (s, 3H), 3.6 (m, 2+2H), 4.2–4.7 (m, 6H), 5.05 (q, 1H), 5.40 (s, broad, 1H), 5.70 (q, 1H), 6.50 (s, 1H), 7.05 (d, 1H), 7.45 (d, 1H), 8.15 (s, 1H).

EXAMPLE 16

Sodium 7α-methoxy-7β-{D-α-[3-(2-(5'-sulfamoyl-2'-thienylmethylamino)-4-hydroxy-5-pyrimidinyl)-ureido]-phenyl-acetamido}-3-[(1-methyl-tetrazol-5-yl)-thiomethyl]-ceph-3-em-4-carboxylate 1.9 gm of 7α-methoxy-7β-(D-α-amino-phenylacetamido)-3-[(1-methyltetrazol-5-yl)-thiomethyl]-ceph-3-em-4-carboxylic acid (0.004 mol) were suspended in a mixture of 60 ml of tetrahydrofuran and 20 ml of water. 1 N sodium hydroxide was added while cooling with ice, and a solution was formed thereby.

A phosgene adduct prepared analogous to Example 10 from 1.2 gm of 5-amino-4-hydroxy-2-(5-sulfamoyl-thienylmethylamino)-pyrimidine (0.004 mol) was added dropwise to this solution, while cooling with ice. The pH was maintained at 8.0 by the addition of sodium hydroxide. The reaction and preparation were continued analogous to Example 10.

Yield: 1.53 gm of sodium salt (46% of theory).
IR-spectrum: 1760, 1660 cm⁻¹.
NMR-spectrum (DMSO+CD₃OD) signals at ppm: 3.4–3.6 (m, 2H), 3.50 (s, 3H), 3.95 (s, 3H), 4.2 (m, 2H), 4.6 (m, 2H), 5.05 (s, 1H), 5.55 (s, 1H), 7.05 (d, 1H), 7.5 (m, 6H), 8.15 (s, 1H).

The following compounds of the formula I (A=phenyl, Y=methoxy, E=hydrogen) were prepared analogous to Example 16:

| Example | R₂ | D | Yield % | IR-Spec. cm⁻¹ | NMR-Spectrum (DMSO + CD₃OD) signals at ppm: |
|---|---|---|---|---|---|
| 17 | H₂NS(O₂)–thienyl–CH₂– | —OCOCH₃ | 54.5 | 1765 1670 | 2.05 (s,3H), 3.5 (s,3H+m,2H), 4.7 (m,2+2H), 5.05 (s,1H), 5.5 (s,1H), 7.05 (d,1H), 7.55 (m,5H+1H), 8.13 (s,1H). |
| 18 | H₂NS(O₂)–thienyl–CH₂– | tetrazolyl-N-CH₂CH₂OH | 38 | 1765 | 3.48 (s,3H), 3.6 (m,2H), 4.3 (m,6H), 4.6 (m,2H), 5.0 (s,1H), 5.55 (s,1H), 7.05 (d,1H), 7.5 (m,6H), 8.15 (s,1H). |
| 19 | furyl-CH₂– | tetrazolyl-N-CH₃ | 51 | 1765 1670 1610 | 3.50 (s,3H), 3.5 (m,2H), 3.95 (s,3H), 4.2–4.4 (m,2H+2H), 5.0 (s,1H), 5.55 (s,1H), 6.3 (m,2H), 7.5 (m, 6H), 8.15 (s,1H). |
| 20 | HO–pyridyl– | tetrazolyl-N-CH₃ | 40 | 1765 1660 | 3.50 (s,3H, m,2H), 3.95 (s,3H), 4.25 (m,2H), 5.05 (s,1H), 5.55 (s,1H), 6.35 (d,1H), 7.5 (m,6H), 7.8 (s,1H), 8.05 (s,1H). |
| 21 | H₂NS(O₂)–pyridyl– | tetrazolyl-N-CH₃ | 34 | 1765 | 3.50 (s,3H+m,2H), 3.95 (s,3H), 4.25 (m,2H), 5.05 (s,1H), 5.55 (s,1H), 7.5 (m,5H+1H), 8.05 (s,1H), 8.2 (m,2H). |
| 22 | furyl-CH₂– | tetrazolyl-N-CH₂CH₂OH | 56 | 1765 1660 1610 | 3.48 (s,3H), 3.4–3.6 (m,2H), 4.3 (m,8H), 5.0 (s,1H), 5.55 (s,1H), 6.3 (m,2H), 7.5 (m,5+1H), 8.10 (s,1H). |

EXAMPLE 23

Sodium 7α-methoxy-7β{D-α-[3-(4-hydroxy-2-(4'-methyl-2'-imidazolylmethylamino)-5-pyrimidinyl)-ureido]-p-hydroxyphenyl-acetamido}-3-[(1-methyl-tetrazol-5-yl)-thiomethyl]-ceph-3-em-4-carboxylate (a) D-α-{3-[4-Hydroxy-2-(4'-methyl-2'-imidazolyl-methylamino)-5-pyrimidinyl]-ureido}-p-hydroxy-phenylacetic acid 1.1 gm (0.005 mol) of 5-amino-4-hydroxy-2-(4'-methyl-2'-imidazolyl-methylamino)-pyrimidine were refluxed in 60 ml of dry tetrahydrofuran with 4 ml of diethylaminotrimethylsilane until a solution was formed. The solution was evaporated to dryness in vacuo, and the residue was taken up in 50 ml of tetrahydrofuran. This solution was added dropwise to a solution of 525 mg of phosgene in tetrahydrofuran, while cooling with ice. After 15 minutes, the mixed solution was concentrated to half its volume in vacuo. This solution was added dropwise at 5° C. to a solution of 850 mg of p-hydroxyphenyl glycine in a mixture of tetrahydrofuran, 10 ml of water and 5 ml of 1 N sodium hydroxide. After it had all been added, the pH was adjusted to 8.0 and the mixture was stirred at room temperature for 1 hour. It was then diluted with 20 ml of water, the tetrahydrofuran was evaporated in vacuo, and the residue was extracted twice with ethyl acetate. The aqueous phase was adjusted to pH 2.9 with 2 N hydrochloric acid while cooling, and the precipitate formed thereby was suction-filtered off and dried.

Yield: 1.45 gm (70.5% of theory).

IR-spectrum: 3350, 1660, 1540, 1530 cm$^{-1}$.

NMR-spectrum (DMSO+CD$_3$OD) signals at ppm: 2.1 (s, 3H), 4.4 (s, 2H), 5.15 (s, 1H), 6.75 (m, 2H+1H), 7.3 (d, 2H), 8.15 (s, 1H).

(b) 1.25 gm (0.003 mol) of the ureidocarboxylic acid thus obtained were dissolved in 40 ml of dry dimethylformamide. First, a solution of 1.5 gm of diphenylmethyl 7-amino-3-[(1-methyl-tetrazol-5-yl)-thiomethyl]-ceph-3-em-4-carboxylate in 20 ml of methylene chloride was added, and then 650 mg of dicyclohexylcarbodiimide were added, while cooling with ice. The mixture was stirred overnight at room temperature and then evaporated to dryness in vacuo. The residue was extracted first with 50 ml of methanol and then with 100 ml of methylene chloride. To remove slight impurities, the product was chromatographed on a silicagel column (eluant: methylene chloride/methanol 5:1). The 7α-unmethoxylated diphenylmethyl ester of the title compound was obtained. Yield: 1.62 gm (62% of theory).

(c) 890 mg of this ester were dissolved in 50 ml of dry tetrahydrofuran. At −70° C., a solution of 240 mg of lithium methoxide in 10 ml of methanol was added, and the mixture was stirred for 3 minutes. Then, at −70° C., 150 mg of t-butyl hypochlorite were added. The mixture was stirred for 45 minutes at −70° C., and then 0.3 ml of glacial acetic acid and 75 mg of triethyl phosphite were added. At room temperature, 70 ml of phosphate buffer were added (pH 7.0), and the mixture was extracted three times with methylene chloride. The organic phase was separated and dried, and the solvent was evaporated in vacuo. The residue was chromatographed on a silicagel column (eluant: methylene chloride/methanol 6:1). 350 mg (38.5% of theory) of the diphenyl ester of the title compound were obtained.

This ester was stirred for 30 minutes with 4 ml of trifluoroacetic acid, 2 ml of anisole and 10 ml of methylene chloride, while cooling with ice. The mixture was then evaporated to dryness in vacuo, and the residue was admixed with ether. The solid product was separated by suction-filtering and treated in a dimethylformamide/methanol mixture with the corresponding amount of sodium hexanoate in order to prepare the sodium salt. The salt was precipitated with ether, suction-filtered off and dried in vacuo.

IR-spectrum: 1765, 1660, 1550 cm$^{-1}$.

NMR-spectrum (DMSO+CD$_3$OD) signals at ppm: 2.1 (s, 3H), 3.45 (s, 3H), 3.55 (m, 2H), 3.95 (s, 3H), 4.35 (m, 4H), 5.0 (s, 1H), 5.40 (s, 1H), 6.75 (m, 2+1H), 7.30 (d, 2H), 8.05 (s, 1H).

The 7α-methoxy-substituted cephalosporins of the formula I shown in the following table were prepared analogous to Example 16 or 23. The synthesis of the corresponding ureidocarboxylic acids and the synthesis of the 7α-H-benzhydryl esters is described in German Offenlegungsschrift No. 2,928,344.

| Example | A | R$_2$ | D | Yield % | IR-Spectrum cm$^{-1}$ | NMR-Spectrum (DMSO + CD$_3$OD) Signals at ppm: |
|---|---|---|---|---|---|---|
| 24 | HO–⟨⟩– | pyridinyl-CH$_2$– | –S–(1-methyl-tetrazol-5-yl) | 33.5 | 1765, 1660, 1540 | 3.45 (s,3H), 3.55 (m,2H), 3.95 (s,3H), 4.25–4.45 (m,4H), 4.95 (s,1H), 5.35 (s,1H), 6.75 (d,2H), 7.25 (m,3H), 7.7 (m,1H), 8.1 (s,1H), 8.5 (m,2H). |
| 25 | HO–⟨⟩– | NH$_2$O$_2$S–thienyl-CH$_2$– | –S–(1-methyl-tetrazol-5-yl) | 41 | 1765, 1655, 1535 | 3.45 (s,3H), 3.55 (m,2H), 3.95 (s,3H), 4.3 (m,2H), 4.65 (s,2H), 5.0 (s,1H), 6.75 (d,2H), 7.05 (d,1H), 7.3 (d,2H), 7.45 (d,1H), 8.15 (s,1H). |
| 26 | HO–⟨⟩– | NH$_2$O$_2$S–thienyl-CH$_2$– | –OCOCH$_3$ | 43 | 1765, 1660, 1540 | 2.05 (s,3H), 3.45 (s,3H), 3.45 (m,2H), 4.7–5.0 (m,2+2+1H), 5.35 (s,1H), 6.75 (d,2H), 7.0–7.45 (m,1+2+1H), 8.10 (s,1H). |

-continued

| Example | A | R_2 | D | Yield % | IR-Spectrum cm$^{-1}$ | NMR-Spectrum (DMSO + CD$_3$OD) Signals at ppm: |
|---|---|---|---|---|---|---|
| 27 | thienyl-D,L | NH$_2$O$_2$S-thienyl-CH$_2$- | -S-(1-methyl-tetrazol-5-yl) | 36 | 1765, 1655, 1540 | 3.45 (s,3H), 3.55 (m,2H), 3.95 (s,3H), 4.3 (m,2H), 4.7 (s,2H), 5.0 (s,1H), 5.70 (s,1H), 7.0 (m,3H), 7.4 (m,2H), 8.1 (s,1H). |
| 28 | thienyl-D,L | NH$_2$O$_2$S-thienyl-CH$_2$- | -S-(1-(2-hydroxyethyl)-tetrazol-5-yl) | 39 | 1765, 1665, 1610, 1540 | 3.45 (s,3H+m,2H), 4.3 (m,6H), 4.65 (s,2H), 4.95 (s,1H), 5.70 (s,1H), 7.0 (m,3H), 7.4 (m,2H), 8.1 (s,1H). |
| 29 | HO-phenyl- | furyl- | -S-(1-methyl-tetrazol-5-yl) | 33 | 1765, 1660, 1550 | 3.45 (s,3H), 3.50 (m,2H), 3.95 (s,3H), 4.40 (m,4H), 4.95 (s,1H), 5.35 (s,1H), 6.3 (m,2H), 6.75 (d,2H), 7.25 (d,2H), 7.45 (s,1H), 8.1 (s,1H). |
| 30 | HO-phenyl- | HO-pyridyl- | -S-(1-methyl-tetrazol-5-yl) | 27 | 1765, 1655, 1540 | 3.45 (s,3H), 3.50 (m,2H), 3.95 (s,3H), 4.3 (m,2H), 4.95 (s,1H), 5.35 (s,1H), 6.55 (s, broad, 1H), 6.75 (d,2H), 7.25 (d,2H), 7.55 (m,1H), 7.8 (d,1H), 8.15 (s,1H). |
| 31 | HO-phenyl- | CH$_3$-pyrimidinyl-CH$_2$- | -S-(1-methyl-tetrazol-5-yl) | 25 | 1765, 1660, 1550 | 2.50 (s,3H), 3.45 (s,3H), 3.55 (m,2H), 3.95 (s,3H), 4.4 (m,4H), 4.95 (s,1H), 5.40 (s,1H), 6.75 (d,2H), 7.25 (d,2H), 8.05 (s,1H), 8.6 (s,2H). |

EXAMPLE 32

Sodium 7α-methoxy-7β-{D-α-[(2-(5′-aminosulfonyl-2′-thienylmethylamino-4-hydroxy-5-pyrimidinyl)-ureido]-p-hydroxyphenyl-acetamido}-3-{[1-(2′-hydroxyethyl)-tetrazol-5-yl]-thiomethyl}-ceph-3-em-4-carboxylate 500 mg of the cephalosporin of Example 26 were heated at 80° C. with 180 mg of 1-(2′-hydroxyethyl)-5-mercaptotetrazole in 40 ml of nitromethane for 6 hours. The mixture was then evaporated to dryness in vacuo. The residue was dissolved in a mixture of acetone and ethyl acetate. While cooling with ice, diphenyldiazomethane was added until the violet color was maintained.

The mixture was then evaporated to dryness. The residue was purified by column chromatography (silicagel; eluant: methylene chloride/methanol 5:1). The ester thus obtained was cleaved as described in Example 1, and the acid was converted into its sodium salt.

Yield of sodium salt: 230 mg.

IR-spectrum: 1765, 1660, 1540, 1155 cm$^{-1}$.

NMR-spectrum (DMSO+CD$_3$OD) signals at ppm: 3.45 (s, 3H), 3.55 (m, 2H), 4.0–4.7 (m, 8H), 5.0 (s, 1H), 5.45 (s, 1H), 6.75 (d, 2H), 7.0 (d, 1H), 7.25 (d, 2H), 7.45 (d, 1H), 8.15 (s, 1H).

The following compound was prepared analogously:

EXAMPLE 33

Sodium 7α-methoxy-7β-{D,L-α-[3-(2-(5′-aminosulfonyl-2′-thienylmethylamino)-4-hydroxy-5-pyrimidinyl)-ureido]-p-hydroxyphenylacetamido}-3-[(2-methyl-1,3,4-thiadiazol-5-yl)-thiomethyl]-ceph-3-em-4-carboxylate Prepared with the cephalosporin of Example 26 and 2-methyl-5-mercapto-1,3,4-thiadiazole.

Yield of sodium salt: 44% of theory.

IR-spectrum: 1765, 1655, 1610, 1540 cm$^{-1}$.

NMR-spectrum (DMSO+CD$_3$OD) signals at ppm: 2.75 (s, 3H), 3.45 (s, 3H), 3.50 (m, 2H), 4.25 (m, 2H), 4.65 (s, 2H), 4.95 (s, 1H), 5.45 (s, 1H), 6.75 (d, 2H), 7.05 (d, 1H), 7.25 (d, 2H), 7.45 (d, 1H), 8.15 (s, 1H).

The compounds of the present invention, that is, those embraced by formulas I and I′ and their non-toxic, pharmacologically acceptable salts, have useful pharmacodynamic properties. More particularly, they exhibit very effective antibacterial activity in warm-blooded animals, such as mice.

Furthermore, the compounds according to the present invention are very well compatible. Therefore they are useful for the prophylaxis and chemotherapy of local and systemic infections in both human and veterinary medicine.

Thus, for example, these compounds are useful for the treatment of diseases of the respiratory tract, the pharyngeal cavity and urinary tract, particularly pharyngitis, pneumonia, peritonitis, pyelonephritis, otitis, cystitis, endocarditis, bronchitis, arthritis and general systemic infections. Moreover, these compounds are useful as preservatives for inorganic or organic materials, especially for organic materials such as polymers, lubricants, dyes, fibers, leather, paper and wood, as well as foodstuffs.

This is made possible by the fact that the compounds of the present invention are highly active, both in vitro and in vivo, against harmful microorganisms, particularly against gram-positive and gram-negative bacteria and bacteria-like microorganisms, being distinguished in particular by a broad spectrum of activity.

Many local and/or systemic bacterial diseases can be treated and/or prevented by used of theses cephalosporin derivatives of the present invention. Examples of such diseases include but are not limited to those caused by the following microorganisms:

Micrococcaceae, such as staphylococci;
Lactobacteriaceae, such as streptococci;
Corynebacteriaceae, such as corynebacteria;
Enterobacteriaceae, such as Escherichiae bacteria of the coli group;
Klebsiella bacteria, such as *K. pneumoniae;*
Proteae bacteria of the proteus group, such as *proteus vulgaris;*
Salmonella bacteria, such as thyphimurium;
Shigella bacteria, such as *shigella dysenteriae;*
Pseudomonas bacteria, such as *pseudomonas aeruginosa;*
Aeromonas bacteria, such as *aeromonas lique faciens;*
Spirillaceae such as vibrio bacteria, such as *vibrio cholerae;*
Parvobacteriaceae or brucellaceae, such as *pasteurella bacteria;*
Brucella bacteria, such as *brucella abortus;*
Neisseriaceae, such as neisseria;
Haemophilus bacteria, such as *haemophilus influenza;*
Bordatella bacteria, such as *bordatella pertussis;*
Moraxella bacteria, such as *moraxella lacunata;*
Bacteroidaceae, such as *bacteroides bacteria;*
Fusiforme bacteria, such as *fusobacterium fusiforme;*
Sphaerophorus bacteria, such as *sphaerophorus necrophorus;*
Bacillaceae, such as aerobic spore formers, like *bacillus antracis;*
Anerobic spore formers chlostridia, such as *chlostridium perfringens;*
Spirochaetaceae, such as *borrelia bacteria;*
Treponema bacteria, such as *treponema palidum;* and
Leptospira bacteria, such as *leptospira interrogans.*

Specific examples of compounds of the present invention, which exhibit broad-spectrum antibacterial activity are those shown in the following table:

TABLE I

Cephalosporins of the formula

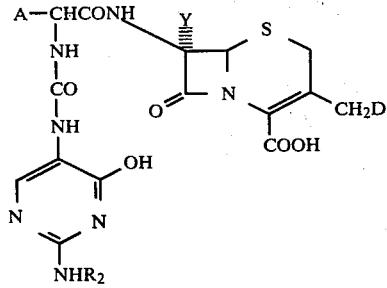

or their sodium salts.

| Compound No. | A | R₂ | Y | D |
|---|---|---|---|---|
| 1 | H₂N-[thiazole] | furan-CH₂— | H | —S-[1-methyl-tetrazole] |
| 2 | H₂N-[thiazole] | HO-pyridine | H | —S-[1-methyl-tetrazole] |
| 3 | H₂N-[thiazole] | H₂NSO₂-thiophene-CH₂— | H | —OCOCH₃ |
| 4 | H₂N-[thiazole] | H₂NSO₂-thiophene-CH₂— | H | —S-[1-methyl-tetrazole] |

TABLE I-continued
Cephalosporins of the formula
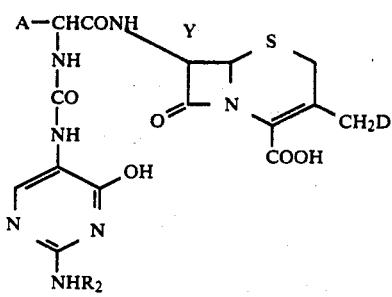
or their sodium salts.
| Compound No. | A | R₂ | Y | D |
|---|---|---|---|---|
| 5 | 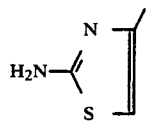 | 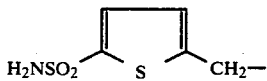 | —OCH₃ | 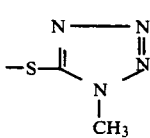 |
| 6 | 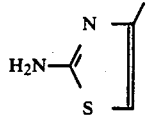 | 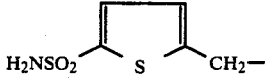 | H | 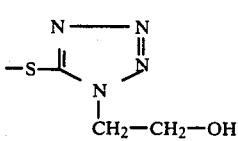 |
| 7 | 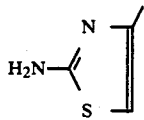 | 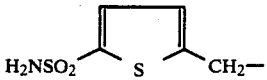 | —OCH₃ | 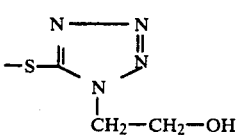 |
| 8 | 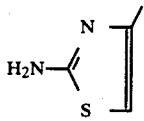 | 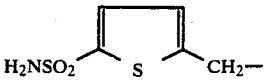 | H | 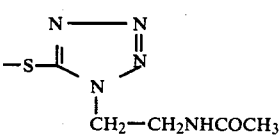 |
| 9 | 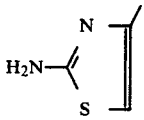 | 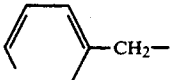 | H | 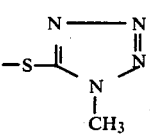 |
| 10 | 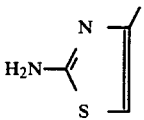 | 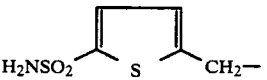 | H | 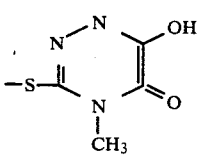 |
| 11 | 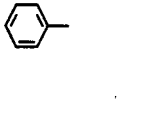 | 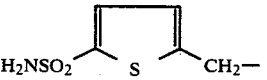 | —OCH₃ | 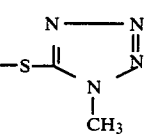 |
| 12 | 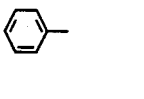 | 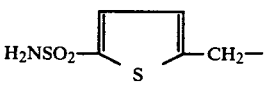 | —OCH₃ | —OCOCH₃ |

TABLE I-continued

Cephalosporins of the formula

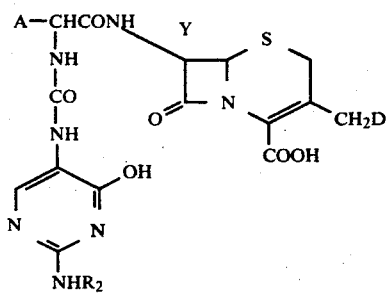

or their sodium salts.

| Compound No. | A | R₂ | Y | D |
|---|---|---|---|---|
| 13 | phenyl- | H₂NSO₂-thiophene-CH₂- | —OCH₃ | —S-(1-methyltetrazole with CH₂CH₂OH on N) |
| 14 | phenyl- | furan-CH₂- | —OCH₃ | —S-(1-methyltetrazole, N-CH₃) |
| 15 | phenyl- | HO-pyridyl- | —OCH₃ | —S-(1-methyltetrazole, N-CH₃) |
| 16 | phenyl- | SO₂NH₂-pyridyl- | —OCH₃ | —S-(1-methyltetrazole, N-CH₃) |
| 17 | phenyl- | furan-CH₂- | —OCH₃ | —S-(1-tetrazole, N-CH₂CH₂OH) |
| 18 | HO-phenyl- | H₂N—SO₂-thiophene-CH₂- | —OCH₃ | —S-(tetrazole, N-CH₂₃CH₂OH) |
| 19 | HO-phenyl- | H₂N—SO₂-thiophene-CH₂- | —OCH₃ | —S-(1-methyltetrazole, N-CH₃) |
| 20 | HO-phenyl- | H₂N—SO₂-thiophene-CH₂- | —OCH₃ | —OCOCH₃ |

TABLE I-continued

Cephalosporins of the formula

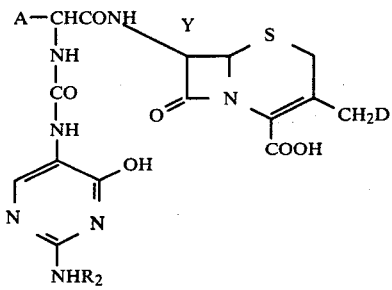

or their sodium salts.

| Compound No. | A | R₂ | Y | D |
|---|---|---|---|---|
| 21 | HO—⟨⟩— | ⟨O⟩—CH₂— | —OCH₃ | —OCOCH₃ |
| 22 | HO—⟨⟩— | ⟨O⟩—CH₂— | —OCH₃ | —S—(tetrazole-N-CH₃) |
| 23 | HO—⟨⟩— | HO—⟨N⟩— | —OCH₃ | —S—(tetrazole-N-CH₃) |
| 24 | ⟨S⟩— | H₂NSO₂—⟨S⟩—CH₂— | —OCH₃ | —S—(tetrazole-N-CH₃) |

The antibiotic activities of the compounds of the present invention were ascertained by the following test methods:

1. In vitro tests

These tests were performed using the serial dilution test in the microtiter system. The effect of the test compound on bacteriostasis was tested in a liquid medium at the following concentrations: 128, 64, 32, 16, 8, 4, 2, 1, 0.5, 0.25, 0.12 and 0.06 μgm/ml. The nutrient medium consisted of 10 gm of peptone, 8 gm of meat extract oxoid, 3 gm of sodium chloride, and 2 gm of sec. sodium phosphate diluted with distilled water to 100 ml (pH 7.2–7.4). The age of the primary cultures was approximately 20 hours. The standardization of the bacteria suspension was effected using a photometer according to the method of Eppendorf (test tube φ 14 mm, filter 546 nm), using for comparison a barium sulfate suspension formed by the addition of 3.0 ml of 1% barium chloride solution to 97 ml of 1% sulfuric acid. After standardization, the test microorganisms were further diluted to a concentration of 1:1500, using a sodium chloride solution.

16 mgm of the particular test compound were put into a 10 ml measuring flask, and the flask was subsequently filled to the mark with the solvent. The further dilution series was standardized with distilled water or the appropriate solvent.

The depressions of the microtiter plates were filled with 0.2 ml of nutrient medium. 0.01 ml of the appropriate test compound solution was then added, followed by inoculation with 0.1 ml (1 drop) of the standardized bacteria suspension. The bacteria were incubated at 37° C. for 18 to 20 hours. Control tests using only the solvent were carried out simultaneously.

The readings were made macroscopically to determine the minimum inhibitory concentration (the lowest still bacteriostatically effective concentration).

The following test organisms were used:

*Staphylococcus aureus* SG 511, *Escherichia coli* ATCC 11 775, *Pseudomonas aeruginosa hamburgensis* and *Pseudomonas aeruginosa* BC 19, *Serratia marcescens* ATCC 13 800, *Klebsiella pneumoniae* ATCC 10031 and BC 6, *Proteus mirabilis* BC 17, *Proteus rettgeri* BC 7, *Enterobacter Cloaceae* ATCC 13047 and *E. coli* R+TEM (β-lactamase carrier).

Table II below shows the minimum inhibiting concentration (MIC) in μgm/ml determined for typical representatives of the compounds according to the invention, where the numbering of the compounds corresponds to that of table I, in comparison to the known cephalosporin cefuroxim:

TABLE II

| Compound No. | Staph. aureus SG 511 | E. coli ATCC 11775 | Pseud. Hbg. | Pseud. BC 19 | Serr. marcesc. ATCC 13880 | Kl. pneum. ATCC 10031 | Kl. pneum. BC 6 | Prot. mirab. BC 17 | Prot. rettg. | Ent. cloac. ATCC 13047 | E. coli R + TEM | K. pneum. 1082 E |
|---|---|---|---|---|---|---|---|---|---|---|---|---|
| | | | | | Minimum inhibiting concentration in μgm/ml | | | | | | | |
| 1 | 1 | 0.03 | 16 | 16 | 0.06 | 0.06 | 0.03 | 0.01 | 0.06 | 0.25 | 0.5 | 16 |
| 4 | 1 | 0.01 | 16 | 8 | 0.06 | 0.03 | 0.03 | 0.01 | 0.01 | 0.06 | 0.25 | 8 |
| 6 | 1 | <0.03 | 16 | 8 | 0.06 | 0.06 | 0.03 | 0.03 | 0.06 | 0.06 | 0.5 | 16 |
| 11 | 1 | 0.12 | 16 | 8 | 0.25 | 0.25 | 0.25 | 0.06 | 0.5 | 0.5 | 0.25 | 0.25 |
| 14 | 0.5 | 0.12 | 8 | 8 | 0.25 | 0.25 | 0.25 | 0.12 | 1 | 1 | 0.25 | 0.25 |
| Cefuroxim | 1 | 8 | >128 | >128 | 8 | 2 | 4 | 0.5 | 2 | 32 | 4 | |

The acute toxicity was determined by oral and subcutaneous administration of the compounds of Table III below at increasing doses to white laboratory mice.

The $LD_{50}$ is the dose which results in the death of 50% of the animals within 8 days. All of the compounds had an $LD_{50}$ of more than 4 gm/kg when administered orally and an $LD_{50}$ of more than 2 gm/kg when administered subcutaneously. The compounds are therefore practically non-toxic.

A few compounds of the invention and cefuroxim were tested in vivo against experimental infections in mice. E. coli ATCC 11775 was used as the pathogenic bacteria. An intraperitoneal infection was induced with 0.2 ml of a 5% mucin suspension of the bacteria. This corresponds to approximately $1.4 \times 10^6$ E. coli bacteria per mouse. Female mice of the NMRI strain were divided into groups of 10 animals, of which 2 groups remained untreated while the remaining groups were treated with various doses of the particular cephalosporin according to the invention for the purpose of determining the $ED_{50}$ (dose at which 50% of the animals survive). The treatment was applied once (1 hour after infection). The observation period was 7 days. The results of these tests are shown in Table III below, where the numbering of the compounds again corresponds to that used in Table I.

TABLE III

| In vivo activity in mice E. coli-infection (s.c. administration): | |
|---|---|
| Compound No. | $ED_{50}$ (mg/kg) |
| 1 | 0.8 |
| 4 | <0.5 |
| 6 | <0.5 |
| 11 | ~5 |
| 14 | 2.5-5 |
| Cefuroxim | >100 |

For pharmaceutical purposes the compounds of the present invention are administered to warm-blooded animals perorally, parenterally, topically or rectally as active ingredients in customary pharmaceutical compositions, that is, compositions consisting essentially of an inert pharmaceutical carrier and an effective amount of the active ingredient, such as tablets, coated tablets, capsules, granulates, suppositories, solutions, suspensions, emulsion, ointments, gels, creams, powders and sprays. The active ingredient or a mixture of different active ingredients of the formula I may be administered to both humans and animals. The daily dose is from 5 to 500 mgm/kg, preferably from 10 to 200 mgm/kg, body weight at intervals of 24 hours, optionally administered in the form of several single doses. A single dose will preferably contain the active ingredient according to the invention in an amount of from 1 to 250, especially 10 to 60 mgm/kg body weight. Depending on the type and body weight of the patient to be treated, on the type and severity of the disease, on the type of preparation and on the route of administration as well as on the period or interval over which the administration takes place; it may, however, be necessary to deviate from the above dosages. Thus, it may be sufficient in some cases to administer less than the above-mentioned amount of active ingredient, while in other cases the above-mentioned amount of active ingredient must be exceeded. The optimum dosage and route of administration of the active ingredients which are necessary in each case can easily be determined by one skilled in the art.

If the new compounds are used as additives for animal feed, they can be administered in the usual concentrations and preparations together with the feed or with the feed preparations or with drinking water. By means of such administration the infection by gram-negative or gram-positive bacteria can be prevented, improved and/or cured, and also a promotion of the growth and an improvement in the utilization of the feed can be achieved.

The compounds of the formulas I and I' can be incorporated as active ingredients into the usual pharmaceutical preparations such as tablets, coated tablets, capsules or ampules. The single dose for adults is generally between 50 and 1000 mgm, preferably 100 to 500 mgm, the daily dose being between 100 and 4000 mgm, preferably 250 to 2000 mgm.

The following examples illustrate a few pharmaceutical dosage unit compositions comprising a compound of the present invention as an active ingredient and represent the best modes contemplated of using the invention.

EXAMPLE 34

Tablets containing sodium 7α-methoxy-7β-{D-α-[3-(4-hydroxy-2-(4'-methyl-2'-imidazolylmethylamino)-5-pyrimidinyl)-ureido]-p-hydroxyphenyl-acetamido}-3-[(1-methyl-tetrazol-5-yl)-thiomethyl]-ceph-3-em-4-carboxylate A mixture consisting of 2 kg of active substance, 5 kg of lactose, 1.8 kg of potato starch, 0.01 kg of magnesium stearate and 0.1 kg of talcum is compressed in the usual way to form tablets, each containing 200 mgm of active substance.

EXAMPLE 35

Coated tablets containing sodium 7α-methoxy-7β-{D-α-[3-(4-hydroxy-2-(4'-methyl-2'-imidazolylmethylamino)-5-pyrimidinyl)-ureido]-p-hydroxyphenyl-acetamido}-3-[(1-methyl-tetrazol-5-yl)-thiomethyl]-ceph-3-em-4-carboxylate Compressed tablets are prepared analogous to Example I and are then covered in the usual way with a coating consisting of sugar, potato starch, talcum and tragacanth.

EXAMPLE 36

Capsules containing sodium 7α-methoxy-7β-{D-α-[3-(4-hydroxy-2-(4'-methyl-2'-imidazolylmethylamino)-5-pyrimidinyl)-ureido]-p-hydroxyphenyl-acetamido}-3-[(1-methyl-tetrazol-5-yl)-thiomethyl]-ceph-3-em-4-carboxylate 5 kg of active substance are filled in hard gelatine capsules in the usual way, each capsule containing 500 mgm of the active substance.

EXAMPLE 37

Dry ampules containing sodium 7α-methoxy-7β-{D-α-[3-(4-hydroxy-2-(4'-methyl-2'-imidazolylmethylamino)-5-pyrimidinyl)-ureido]-p-hydroxyphenyl-acetamido}-3-[(1-methyl-tetrazol-5-yl)thiomethyl]-ceph-3-em-4-carboxylate Under aseptic conditions, 251 gm of active substance are dissolved in 200 ml of distilled water for injection. The solution is filtered through a Millipore filter (pore size 0.22 ηm). 2.0 ml amounts of the solution are poured into 1000 vials (capacity 10 ml) and lyophilization is carried out. The vials are then sealed with a rubber stopper and an aluminum cover. In this way vials (No. A) are obtained, each containing 250 mgm of active substance.

A physiological saline solution for injection is poured into ampules in amounts of 2.0 ml; and the ampules are sealed. In this way, ampules (No. B) are obtained. The physiological saline solution in the ampules (No. B) is poured into the vials (No. A), thus producing an injectable preparation suitable for intravenous administration.

Distilled water for injection is poured into the vials (No. A) in amounts of 20 ml, and the solution is dissolved in a 5% solution of glucose for injections (250 ml). In this way solutions for continuous infusion are prepared.

Any one of the other compounds embraced by formula I or a non-toxic, pharmacologically acceptable salt thereof may be substituted for the particular ingredients in Examples 34 through 37. Likewise, the amount of active ingredient in these illustrative examples may be varied to achieve the dosage unit range set forth above, and the amount and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

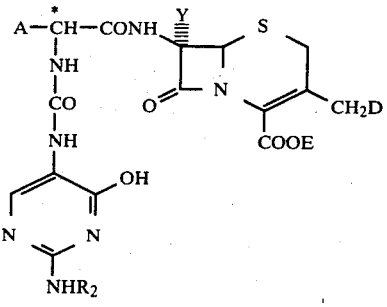

or

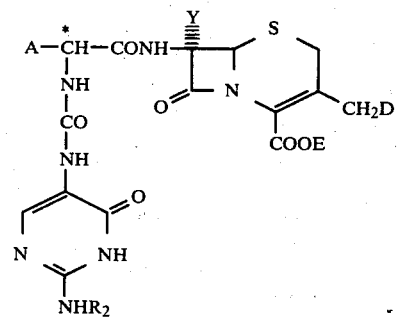

wherein
Y is hydrogen or methoxy;
A is

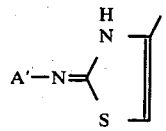

or, when Y is methoxy, also phenyl, 4-hydroxyphenyl, 2-thienyl, 3-thienyl or 3,4-dihydroxy-phenyl;
A' is hydrogen, $-COCH_2Cl$, $-COCH_2Br$, $-COOCH_2CCl_3$, formyl or trityl;
D is hydrogen, acetoxy, aminocarbonyloxy, pyridinium, 4-aminocarbonyl-pyridinium or -S-Het, where Het is 3-methyl-1,2,4-thiadiazol-5-yl, 1,2,4-thiadiazol-5-yl, 1,3,4-thiadiazol-5-yl, 2-methyl-1,3,4-thiadiazol-5-yl, 4H-5,6-dioxo-1,2,4-triazin-3-yl, 4-methyl-5,6-dioxo-1,2,4-triazin-3-yl, 1-vinyl-tetrazol-5-yl, 1-allyl-tetrazol-5-yl or

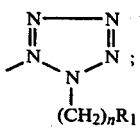

n is 1, 2 or 3;
$R_1$ is hydroxyl, amino, dimethylamino, acetylamino, aminocarbonyl, aminocarbonylamino, aminosulfonyl, aminosulfonylamino, methylcarbonyl, methylsulfonylamino, cyano, hydroxysulfonylamino, methylsulfonyl, methylsulfinyl, a carboxylic acid group or a sulfonic acid group; or
$-(CH_2)_nR_1$ is alkyl of 1 to 4 carbon atoms or 2,3-dihydroxy-propyl;

R₂ is an unsubstituted or monosubstituted radical selected from the group consisting of 3-pyridyl, 5-pyrimidinyl, 2-thienyl, 2-furyl-methyl, 2-thienyl-methyl, 2-imidazolyl-methyl, 2-thiazolyl-methyl, 3-pyridyl-methyl or 5-pyrimidinyl-methyl, where the substituent is chlorine, methyl, acetylamino, hydroxyl, methylsulfinyl, methylsulfonyl, aminocarbonyl or aminosulfonyl; and E is hydrogen or a carboxyl-protective group which is easily removable in vitro or in vivo, or, when E is hydrogen, a non-toxic, pharmacologically acceptable salt thereof formed with an inorganic or organic base.

2. A compound of claim 1, where
A, Y, E and R₂ have the meanings defined in claim 1,
A' is hydrogen; and
D is acetoxy or -SHet, where Het is 2-methyl-1,3,4-thiadiazol-5-yl, 4-methyl-5,6-dioxo-1,2,4-triazin-3-yl or

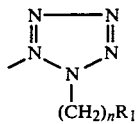

where R₁, n and —(CH₂)ₙR₁ have the meanings defined in claim 1;

or, when E is hydrogen, a non-toxic, pharmacologically acceptable salt thereof formed with an inorganic or organic base.

3. A compound of claim 1, which is
7β-{D,L-α-[3-(4-hydroxy-2-(2'-furylmethylamino)-5-pyrimidinyl)-ureido]-(2,3-dihydro-2-imino-4-thiazolyl)-acetamido}-3-[(1-methyl-tetrazol-5-yl)-thiomethyl]-ceph-3-em-4-carboxylic acid or a nontoxic, pharmacologically acceptable salt thereof formed with an inorganic or organic base.

4. A compound of claim 1, which is
7β-{D,L-α-[3-(2-(5'-aminosulfonyl-2'-thienyl methylamino)-4-hydroxy-5-pyrimidinyl)-ureido]-2,3-dihydro-2-imino-4-thiazolyl)-acetamido}-3-[(1-methyl-tetrazol-5-yl)-thiomethyl]-ceph-3-em-4-carboxylic acid or a non-toxic, pharmacologically acceptable salt thereof formed with an inorganic or organic base.

5. A compound of claim 1 which is
7β-{D,L-α-[3-(2-(5'-aminosulfonyl-2'-thienylmethylamino)-4-hydroxy-5-pyrimidinyl)-ureido]-(2,3-dihydro-2-imino-4-thiazolyl)-acetamido}-3-{[1-(2'-hydroxyethyl)-tetrazol-5-yl]-thiomethyl}-ceph-3-em-4-carboxylic acid or a non-toxic, pharmacologically acceptable salt thereof formed with an inorganic or organic base.

6. A compound of claim 1, which is
7α-methoxy-7β-[D,L-α-[3-(2-(5'-aminosulfonyl-2'-thienylmethylamino)-4-hydroxy-5-pyrimidinyl)-ureido]-phenylacetamido}-3-[(1-methyl-tetrazol-5-yl)-thiomethyl]-ceph-3-em-4-carboxylic acid or a non-toxic, pharmacologically acceptable salt thereof formed with an inorganic or organic base.

7. A compound of claim 1, which is
7α-methoxy-7β-{D,L-α-[3-(2'-furylmethylamino)-5-pyrimidinyl)-ureido]-phenylacetamido}-3-[(1-methyl-tetrazol-5-yl)-thiomethyl]-ceph-3-em-4-carboxylic acid or a non-toxic, pharmacologically acceptable salt thereof formed with an inorganic or organic base.

8. A compound of claim 1, where
A, D and R₂ have the meanings defined in claim 1, and
E is benzyl, diphenylmethyl, trityl, tert. butyl, 2,2,2-trichloroethyl, trimethylsilyl or alkanoyloxyalkyl of 3 to 8 carbon atoms.

9. An antibiotic pharmaceutical composition consisting essentially of an inert pharmaceutical carrier and an effective antibiotic amount of a compound of claim 1.

10. The method of inhibiting the growth of or destroying pathogenic bacteria in a warm-blooded animal in need thereof, which comprises perorally, parenterally, rectally or topically administering to said animal an effective antibiotic amount of a compound of claim 1.

* * * * *

UNITED STATES PATENT AND TRADEMARK OFFICE
CERTIFICATE OF CORRECTION

PATENT NO. : 4,364,944
DATED : December 21, 1982
INVENTOR(S) : BERND WETZEL ET AL.

It is certified that error appears in the above—identified patent and that said Letters Patent is hereby corrected as shown below:

Abstract [57], 4th last line: "E is hydrogen" should read -- when E is hydrogen --.

Column 2, line 26: "pivaloylox-" should be -- pivaloyloxy- --

Column 2, line 27: "ymethyl" should read -- methyl --.

Column 7, line 1: "accordng" should read -- according --.

Column 9, line 26: "know" should read -- known --.

Column 13, line 4: "thieny" should read -- thienyl- --.

Column 13, line 5: "lmethylamino" should read -- methylamino --.

Column 13, line 30: "NM-spectrum" should read -- NMR-spectrum --

Column 13, line 37: Delete "t".

Column 13, line 38: "hienylmethylamino" should read -- thienylmethylamino --.

Column 14, line 22: Delete "i".

Column 14, line 23: "midazolyl" should read -- imidazolyl --.

Column 14, line 62: "thienylmethylamino" should read -- thienylmethylamino)- --.

UNITED STATES PATENT AND TRADEMARK OFFICE
CERTIFICATE OF CORRECTION

PATENT NO. : 4,364,944
DATED : December 21, 1982
INVENTOR(S) : BERND WETZEL ET AL.

It is certified that error appears in the above-identified patent and that said Letters Patent is hereby corrected as shown below:

Column 14, line 63: Delete ")-".
Column 19, line 44: "7β=" should read -- 7β- --.
Column 19, line 45: "t-hienylmethylamino" should read -- thienylmethylamino --.
Column 25/26, Example 15: Correct the formula in column D to read --

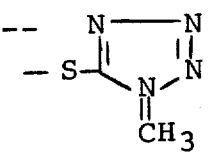

--.

Column 25/26, Example 18: The portion of the formula in column d which reads "CH$_{23}$CH$_2$OH" should read -- CH$_2$CH$_2$OH --.
Column 31, line 27: "0.22 ηm" should read -- 0.22 μm --.

Signed and Sealed this

Sixteenth Day of August 1983

[SEAL]

Attest:

GERALD J. MOSSINGHOFF

Attesting Officer    Commissioner of Patents and Trademarks